(12) United States Patent
McEneany et al.

(10) Patent No.: US 11,724,002 B2
(45) Date of Patent: Aug. 15, 2023

(54) TECHNIQUE FOR FORMING POROUS FIBERS

(71) Applicant: Kimberly-Clark Worldwide, Inc., Neenah, WI (US)

(72) Inventors: Ryan J. McEneany, Appleton, WI (US); Vasily A. Topolkaraev, Appleton, WI (US); Yuewen Xu, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1021 days.

(21) Appl. No.: 16/470,858

(22) PCT Filed: Jan. 19, 2018

(86) PCT No.: PCT/US2018/014397
§ 371 (c)(1),
(2) Date: Jun. 18, 2019

(87) PCT Pub. No.: WO2018/160284
PCT Pub. Date: Sep. 7, 2018

(65) Prior Publication Data
US 2019/0374672 A1 Dec. 12, 2019

Related U.S. Application Data

(60) Provisional application No. 62/464,569, filed on Feb. 28, 2017.

(51) Int. Cl.
*D01D 5/08* (2006.01)
*D01D 5/088* (2006.01)
(Continued)

(52) U.S. Cl.
CPC .............. *A61L 15/26* (2013.01); *C08L 67/02* (2013.01); *D01D 5/247* (2013.01); *D01F 1/08* (2013.01);
(Continued)

(58) Field of Classification Search
CPC .......... D01D 5/08; D01D 5/088; D01D 5/247; D01F 1/08; D01F 6/04; D01F 6/06;
(Continued)

(56) References Cited

U.S. PATENT DOCUMENTS 5,192,308 A 3/1993 Ostapchenko
5,354,532 A 10/1994 Nakai et al.
(Continued)

FOREIGN PATENT DOCUMENTS

CN 103981635 8/2014
CN 105246443 A 1/2016
(Continued)

OTHER PUBLICATIONS

Chinese Office Action Corresponding to Application No. 201880010566 dated Jun. 22, 2021.
(Continued)

*Primary Examiner* — Leo B Tentoni
(74) *Attorney, Agent, or Firm* — Dority & Manning, P.A.

(57) ABSTRACT

A method for forming a fiber is provided. The method comprises extruding a matrix polymer and a nanoinclusion additive to form a thermoplastic composition in which the nanoinclusion additive is dispersed within a continuous phase of the matrix polymer. The extruded thermoplastic composition is thereafter passed through a spinneret to form a fiber having a porous network containing a plurality of nanopores, wherein the average percent volume occupied by the nanopores within a given unit volume of the fiber is from about 3% to about 15% per $cm^3$.

20 Claims, 2 Drawing Sheets

(51) Int. Cl.
| | |
|---|---|
| *D01F 6/06* | (2006.01) |
| *A61L 15/26* | (2006.01) |
| *C08L 67/02* | (2006.01) |
| *D01D 5/247* | (2006.01) |
| *D01F 1/08* | (2006.01) |
| *D01F 6/04* | (2006.01) |
| *D01F 6/62* | (2006.01) |

(52) U.S. Cl.
CPC ............... *D01F 6/04* (2013.01); *D01F 6/62* (2013.01); *C08L 2203/12* (2013.01); *C08L 2205/025* (2013.01); *D10B 2321/02* (2013.01); *D10B 2321/021* (2013.01); *D10B 2331/04* (2013.01); *D10B 2401/10* (2013.01); *D10B 2509/026* (2013.01)

(58) Field of Classification Search
CPC . D01F 6/62; D10B 2321/02; D10B 2321/021; D10B 2331/04; D10B 2401/10
USPC .................................. 264/210.6, 211, 211.14
See application file for complete search history.

(56) References Cited

U.S. PATENT DOCUMENTS

| | | | |
|---|---|---|---|
| 6,548,431 | B1 | 4/2003 | Bansal et al. |
| 2005/0260911 | A1 | 11/2005 | Ochi et al. |
| 2005/0272897 | A1* | 12/2005 | Prasad .................. C08G 77/06 528/31 |
| 2008/0125551 | A1 | 5/2008 | Vollenberg |
| 2012/0231690 | A1 | 9/2012 | Pourdeyhimi et al. |
| 2013/0210308 | A1 | 8/2013 | McEneany et al. |
| 2015/0318067 | A1 | 11/2015 | Asano et al. |
| 2016/0108564 | A1* | 4/2016 | Topolkaraev .......... D01D 5/247 442/338 |
| 2016/0130731 | A1* | 5/2016 | Topolkaraev ............. D01F 6/06 521/134 |
| 2016/0177048 | A1 | 6/2016 | Topolkaraev et al. |
| 2019/0374672 | A1 | 12/2019 | McEneany et al. |

FOREIGN PATENT DOCUMENTS

| | | | | |
|---|---|---|---|---|
| CN | 105247119 | A | 1/2016 | |
| CN | 105263994 | A | 1/2016 | |
| CN | 105263997 | A | 1/2016 | |
| EP | 1878482 | A1 | 1/2008 | |
| JP | H10259519 | A | 9/1998 | |
| KR | 1020020061648 | | 7/2002 | |
| WO | WO2014199269 | | 12/2014 | |
| WO | WO-2014199274 | A1 * | 12/2014 | ............ D01D 5/247 |
| WO | WO2016100057 | | 6/2016 | |

OTHER PUBLICATIONS

Chinese Search Report Corresponding to Application No. 2018800105669 dated Jun. 16, 2021.
International Search Report for PCT/US2018/014397 dated Aug. 24, 2018, 12 pages.
Korean Office Action Corresponding to Application No. 1020197025620 dated May 25, 2022.
The Chinese Office Action Corresponding to Application No. 201880010566 dated Jul. 21, 2022.
The Chinese Search Report Corresponding to Application No. 201880010566 dated Jul. 21, 2022.
Australian Office Action Corresponding to Application No. 2018228336 dated Dec. 13, 2022.

\* cited by examiner

TECHNIQUE FOR FORMING POROUS FIBERS

RELATED APPLICATIONS

The present application is the national stage entry of International Patent Application No. PCT/US2018/014397 having a filing date of Jan. 19, 2018, which claims priority to U.S. provisional application Ser. No. 62/464,569, filed on Feb. 28, 2017, which are incorporated herein in their entirety by reference thereto.

BACKGROUND OF THE INVENTION

Significant efforts have been made to produce low density fibers to improve the use of natural resources and reduction of the carbon footprint in finished products. A typical approach to producing such low density fibers is by foaming the polymer using physical or chemical blowing agents, which create gas-filled pores though the bulk. Chemical blowing agents are compounds that undergo chemical reaction liberating gas that creates the pore structure through the bulk of the polymer. Physical blowing agents are typically compressed gases that are dispersed in the polymer and expand creating the pores. Regardless, typical foaming processes induce low molecular orientation because the pore formation happens when the polymer is in the molten state. This prevents the polymer from strain hardening, which typically occurs at temperatures well above the melting temperature or glass transition temperature of the polymer, yielding products with low mechanical strength. Furthermore, typical foaming processes generate large cell sizes, such as greater than 100 µm. This reduces the melt strength, thus leading to breaks in high speed production processes with high deformation rates (e.g., fiber spinning, film formation, molding, etc.).

As such, a need currently exists for an improved process for forming low density, porous fibers.

SUMMARY OF THE INVENTION

In accordance with one embodiment of the present invention, a method for forming a fiber is disclosed that comprises extruding a matrix polymer and a nanoinclusion additive to form a thermoplastic composition in which the nanoinclusion additive is dispersed within a continuous phase of the matrix polymer. Thereafter, the extruded thermoplastic composition is passed through a spinneret to form a fiber having a porous network containing a plurality of nanopores, wherein the average percent volume occupied by the nanopores within a given unit volume of the fiber is from about 3% to about 15% per cm$^3$.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
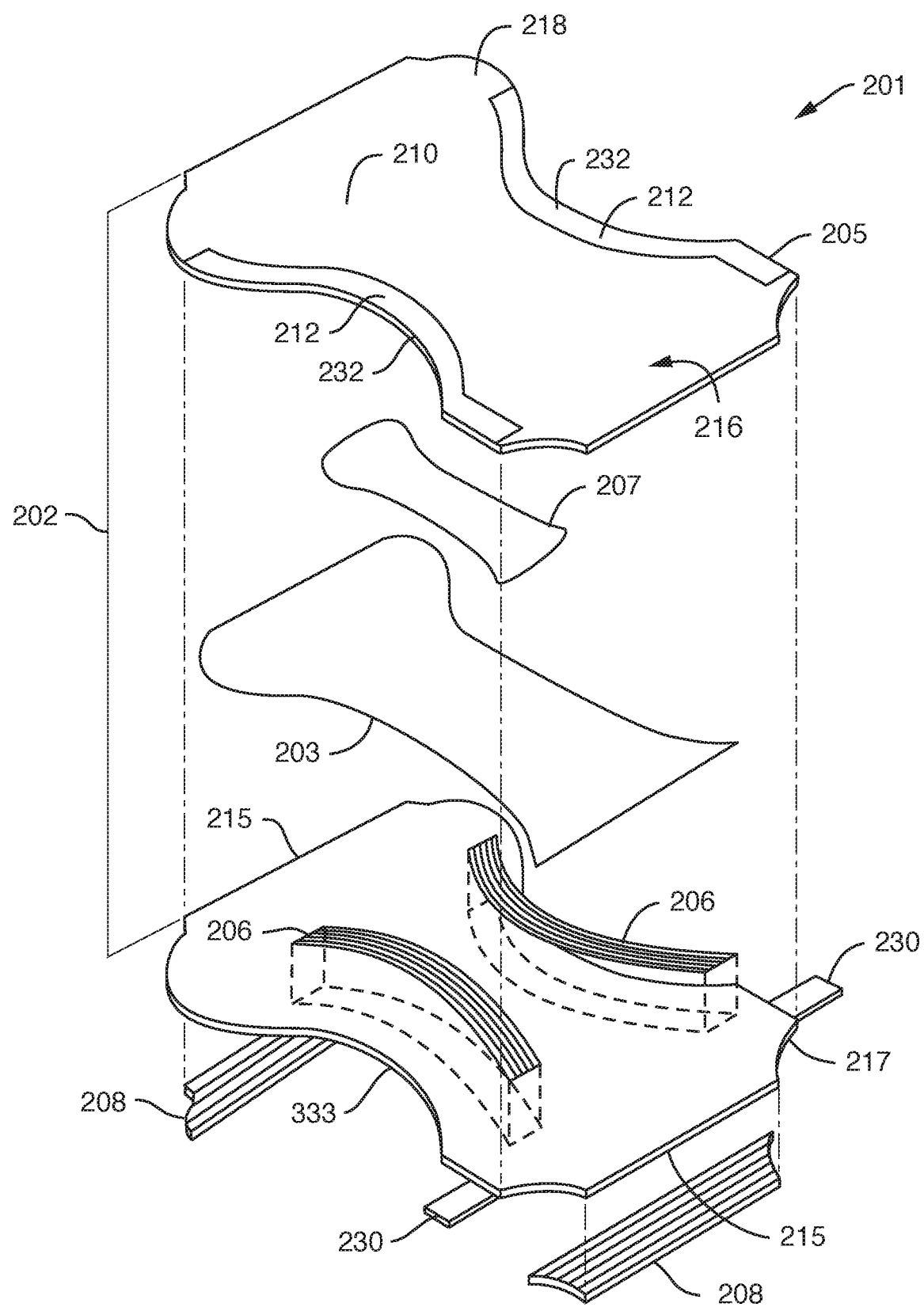
FIG. 1 is a perspective view of one embodiment of an absorbent article that can employ the fibers of the present invention.

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a method for melt drawing a thermoplastic composition during the fiber formation process so that a porous network is formed therein. More particularly, a thermoplastic composition is initially extruded to form a continuous phase, which includes a matrix polymer, and a nanoinclusion additive. Thereafter, the extruded composition is passed through a spinneret to form a fiber. In this regard, as the composition is being passed through the spinneret, the present inventors have discovered that the nano-scale phase domains formed by the nanoinclusion additive are able to interact in a unique manner to create a network of pores. Namely, it is believed that the strain imparted within the spinneret process can initiate intensive localized shear zones and/or stress intensity zones (e.g., normal stresses) near the discrete phase domains as a result of stress concentrations that arise from the incompatibility of the nanoinclusion additive and the matrix polymer. These shear and/or stress intensity zones cause some initial debonding in the matrix polymer adjacent to the domains. Once initial pores are formed, the matrix located between domains can deform plastically to create internal stretched areas that locally narrow (or neck) and strain-harden. This process allows the formation of pores through the bulk of the composition that grow in the stretching direction, thereby leading to the formation of a porous network while the molecular orientation leads to strain-hardening that enhances mechanical strength.

Without intending to be limited by theory, the present inventors believe that such a stable porous network can be achieved due in part to selective control over the melt viscosity (or conversely melt flow rate) between the nanoinclusion additive and matrix polymer. More particularly, the use of a nanoinclusion additive having a higher melt viscosity (lower melt flow rate) than the matrix polymer can help achieve a certain degree of flow instability within the spinneret, which causes pores to form therein. For example, the ratio of the melt flow rate of the matrix polymer to the melt flow rate of the nanoinclusion additive may be about 2:1 or more, in some embodiments from about 2.5:1 to about 10:1, and in some embodiments, from about 3:1 to about 8:1, as determined at the processing temperature. The nanoinclusion additive may, for example, have a melt flow rate (on a dry basis) of from about 0.1 to about 50 grams per 10 minutes, in some embodiments from about 0.5 to about 30 grams per 10 minutes, and in some embodiments, from about 5 to about 15 grams per 10 minutes, determined at a load of 2160 grams and at a temperature at least about 40° C. above the melting temperature (e.g., at 190° C.) in accordance with ASTM D1238-13. The matrix polymer (e.g., polyester) may likewise have a melt flow rate (on a dry basis) of from about 0.5 to about 80 grams per 10 minutes, in some embodiments from about 1 to about 40 grams per 10 minutes, and in some embodiments, from about 5 to about 20 grams per 10 minutes, determined at a load of 2160 grams and at a temperature at least about 40° C. above the melting temperature (e.g., at 260° C. for certain polyesters) in accordance with ASTM D1238-13.

Figure 2:
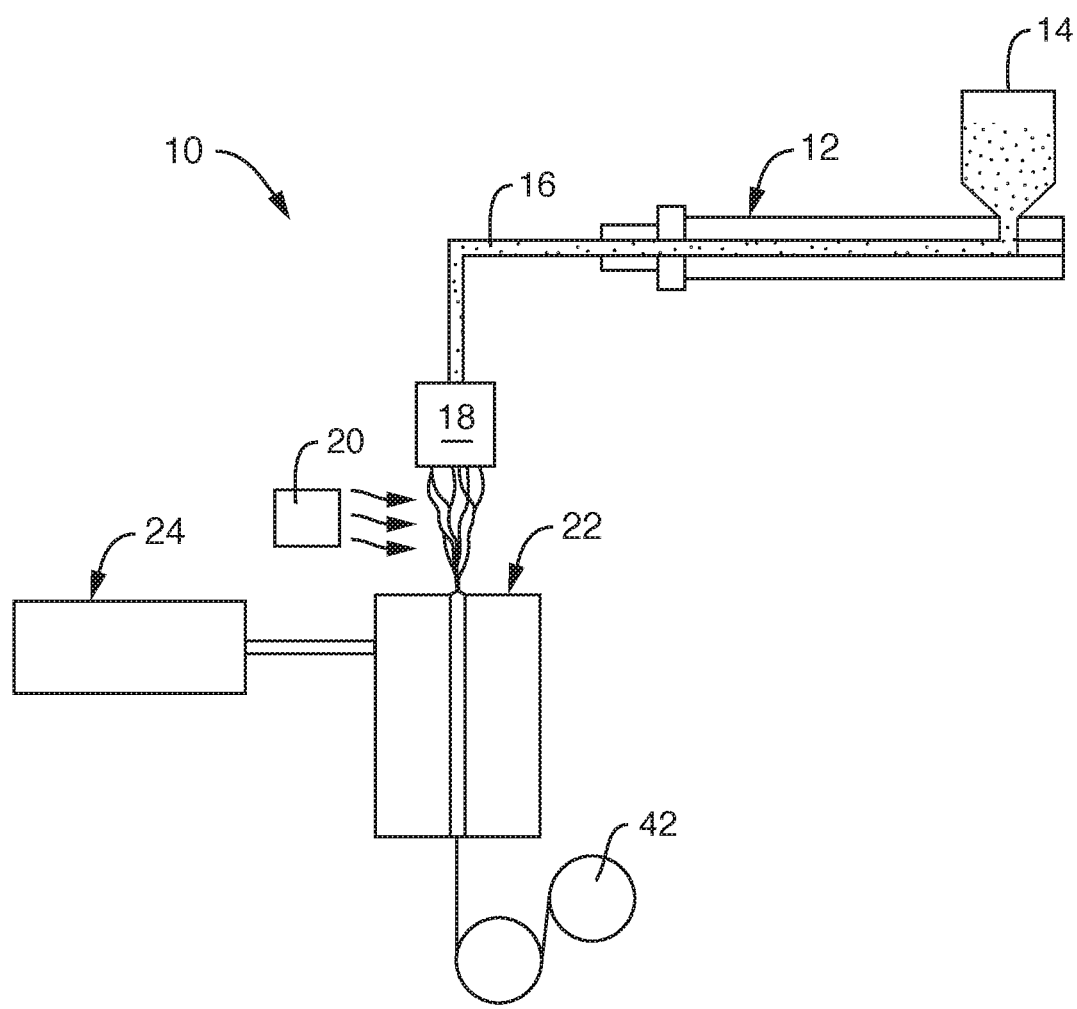
FIG. 2 is a schematic illustration of a process that may be used in one embodiment of the present invention to form fibers.

Referring to FIG. 2, for example, one embodiment of a method for melt drawing a composition into the form of fibers is shown in more detail. In this particular embodiment, the thermoplastic composition may be fed into an extruder 12 from a hopper 14. The blend may be provided to the hopper 14 using any conventional technique. Any conventional extruder may be employed, such as a single-screw extruder, twin-screw extruder, etc. A particularly suitable extruder is a co-rotating, twin-screw extruder (e.g., ZSK-30 extruder available from Werner & Pfleiderer Corporation of Ramsey, N.J. or a Thermo Prism™ USALAB 16 extruder available from Thermo Electron Corp., Stone, England). Such extruders may include feeding and venting ports and provide high intensity distributive and dispersive mixing. For example, the components may be fed to the same or different feeding ports of the twin-screw extruder and melt blended to form a substantially homogeneous melted mixture. If desired, other additives may also be injected into the polymer melt and/or separately fed into the extruder at a different point along its length. While the temperature may vary depending on the melting temperature of the matrix polymer, extrusion and melt drawing typically occur at a temperature of from about 180° C. to about 340° C., in some embodiments from about 185° C. to about 330° C., and in some embodiments, from about 190° C. to about 320° C.

Referring again to FIG. 2, the extruder 12 is heated to a temperature sufficient to extrude the melted polymer. The extruded composition is then passed through a polymer conduit 16 to a spinneret 18. For example, the spinneret 18 may include a housing containing a spin pack having a plurality of plates stacked one on top of each other and having a pattern of openings arranged to create flow paths for directing polymer components. The spinneret 18 also has openings arranged in one or more rows. As discussed above, passage of the composition through the extruder 12 and the spinneret 18 results in the formation of a porous network. Alternatively, the spinneret can be circular in nature with a single or multiple concentric rings of openings. Regardless, to help facilitate the formation of a porous network, the spinneret typically has a length-to-diameter (L/D) ratio of about 6:1 or less, in some embodiments about 4:1 or less, and in some embodiments, from about 0.5:1 to about 2.5:1

The process 10 may also employ a quench blower 20 positioned adjacent the curtain of fibers extending from the spinneret 18. Air from the quench air blower 20 quenches the fibers extending from the spinneret 18 and stabilizes the porous network previously formed during melt drawing. The quench air may be directed from one side of the fiber curtain as shown in FIG. 2 or both sides of the fiber curtain. Alternatively, the quench air can be delivered uniformly in a circular curtain around the outer edge of the fibers (in flow quench) or from the center of the fiber bundle (out flow quench). To form a fiber with the desired length, the quenched fibers are generally melt drawn, such as using a fiber draw unit 22 as shown in FIG. 2. Fiber draw units or aspirators for use in melt spinning polymers are well-known in the art. Suitable fiber draw units for use in the process of the present invention include a linear fiber aspirator of the type shown in U.S. Pat. Nos. 3,802,817 and 3,423,255. The fiber draw 22 generally includes an elongated vertical passage through which the fibers are drawn by aspirating air entering from the sides of the passage and flowing downwardly through the passage. A heater or blower 24 supplies aspirating air to the fiber draw unit 22. The aspirating air melt draws the fibers and ambient air through the fiber draw unit 22. The flow of gas causes the fibers to melt draw or attenuate, which increases the molecular orientation or crystallinity of the polymers forming the fibers. Alternatively, the fibers may be mechanically drawn to create orientation using single godet or series of godet rolls at a take-up speed greater than the linear extrusion speed of the molten polymer exiting the spinneret.

When employing a fiber draw unit, the "draw down" ratio may be selected to help achieve the desired fiber length. The "drawn down" ratio is the linear speed of the fibers after drawing (e.g., linear speed of the godet roll 42 or a foraminous surface (not shown) divided by the linear speed of the fibers after extrusion). For example, the draw down ratio during melt drawing may be calculated as follows:

$$\text{Draw Down Ratio} = A/B$$

wherein,

A is the linear speed of the fiber after melt drawing (e.g., godet speed) and is directly measured; and B is the linear speed of the extruded fiber and can be calculated as follows:

$$\text{Extruder linear fiber speed} = C/(25 * \pi * D * E^2)$$

wherein,

C is the throughput through a single hole (grams per minute);

D is the melt density of the polymer (grams per cubic centimeter); and

E is the diameter of the orifice (in centimeters) through which the fiber is extruded. In certain embodiments, the draw down ratio may be from about 2:1 to about 5000:1, in some embodiments from about 5:1 to about 4000:1, in some embodiments from about 10:1 to about 3000:1, and in some embodiments, from about 15:1 to about 2000:1.

Once formed, the fibers may be deposited through the outlet opening of the fiber draw unit 22 and onto a godet roll 42. If desired, the fibers collected on the godet roll 42 may optionally be subjected to additional in line processing and/or converting steps (not shown) as will be understood by those skilled in the art. For example, fibers may be collected and thereafter crimped, texturized, and/or cut to an average fiber length in the range of from about 3 to about 80 millimeters, in some embodiments from about 4 to about 65 millimeters, and in some embodiments, from about 5 to about 50 millimeters.

Through the techniques noted above, a stable porous network may be formed so that the average percent volume occupied by the nanopores within a given unit volume of the fiber may be from about 3% to about 15% per $cm^3$, in some embodiments from about 4% to about 12%, and in some embodiments, from about 5% to about 10% per cubic centimeter of the material. With such a pore volume, the composition may have a relatively low density. Polyolefin compositions may, for instance, have a density of about 0.92 grams per cubic centimeter ("$g/cm^3$") or less, in some embodiments about 0.90 $g/cm^3$ or less, in some embodiments about 0.88 g/cm³ or less, in some embodiments from about 0.10 g/cm³ to about 0.85 g/cm³, and in some embodiments, from about 0.20 g/cm³ to about 0.80 g/cm³. Likewise, polyester compositions may have a density of about 1.5 g/cm³ or less, in some embodiments from about 0.4 to about 1.4 g/cm³, and in some embodiments, from about 0.5 to about 1.2 g/cm³. A substantial portion of pores in the porous network are also of a "nano-scale" size ("nanopores"), such as those having an average cross-sectional dimension of about 800 nanometers or less, in some embodiments from about 5 to about 700 nanometers, and in some embodiments, from about 10 to about 500 nanometers. The term "cross-sectional dimension" generally refers to a characteristic dimension (e.g., width or diameter) of a pore, which is substantially orthogonal to its major axis (e.g., length) and also typically substantially orthogonal to the direction of the stress applied during drawing. The nanopores may also have an average axial dimension within the range of from about 100 to about 5,000 nanometers, in some embodiments from about 50 to about 2,000 nanometers, and in some embodiments, from about 100 to about 1,000 nanometers. The "axial dimension" is the dimension in the direction of the major axis (e.g., length), which is typically in the direction of drawing. Such nanopores may, for example, constitute about 15 vol. % or more, in some embodiments about 20 vol. % or more, in some embodiments from about 30 vol. % to 100 vol. %, and in some embodiments, from about 40 vol. % to about 90 vol. % of the total pore volume in the fibers. Micropores may also be formed during drawing that have an average cross-sectional dimension of about 0.2 micrometers or more, in some embodiments about 0.5 micrometers or more, and in some embodiments, from about 0.5 micrometers to about 5 micrometers. In certain cases, the axial dimension of the micropores and/or nanopores may be larger than the cross-sectional dimension so that the aspect ratio (the ratio of the axial dimension to the cross-sectional dimension) is from about 1 to about 30, in some embodiments from about 1.1 to about 15, and in some embodiments, from about 1.2 to about 5. For example, the axial dimension of the micropores may be 1 micrometer or more, in some embodiments about 1.5 micrometers or more, and in some embodiments, from about 2 to about 30 micrometers.

Regardless of their particular size, the pores (e.g., nanopores, micropores, or both) can be distributed in a substantially homogeneous fashion throughout the material. For example, the pores may be distributed in columns that are oriented in a direction generally perpendicular to the direction in which a stress is applied. These columns may be generally parallel to each other across the width of the material. Without intending to be limited by theory, it is believed that the presence of such a homogeneously distributed porous network can result in good mechanical properties (e.g., energy dissipation under load and impact strength). This is in stark contrast to conventional techniques for creating pores that involve the use of blowing agents, which tend to result in an uncontrolled pore distribution and poor mechanical properties.

Various embodiments of the present invention will now be described in more detail.

I. Thermoplastic Composition

A. Matrix Polymer

As indicated above, the thermoplastic composition contains a continuous phase within which a nanoinclusion additive is dispersed. The continuous phase contains one or more matrix polymers, which typically constitute from about 60 wt. % to about 99 wt. %, in some embodiments from about 75 wt. % to about 98 wt. %, and in some embodiments, from about 80 wt. % to about 95 wt. % of the thermoplastic composition. The nature of the matrix polymer(s) used to form the continuous phase is not critical and any suitable polymer may generally be employed, such as polyesters, polyolefins, styrenic polymers, polyamides, etc.

In certain embodiments, for instance, a polyolefin may be employed as a matrix polymer. Polyolefins typically have a melting temperature of from about 100° C. to about 220° C., in some embodiments from about 120° C. to about 200° C., and in some embodiments, from about 140° C. to about 180° C., such as determined using differential scanning calorimetry ("DSC") in accordance with ASTM D-3417. Suitable polyolefins may, for instance, include ethylene polymers (e.g., low density polyethylene ("LDPE"), high density polyethylene ("HDPE"), linear low density polyethylene ("LLDPE"), etc.), propylene homopolymers (e.g., syndiotactic, atactic, isotactic, etc.), propylene copolymers, and so forth. In one particular embodiment, the polymer is a propylene polymer, such as homopolypropylene or a copolymer of propylene. The propylene polymer may, for instance, be formed from a substantially isotactic polypropylene homopolymer or a copolymer containing equal to or less than about 10 wt. % of other monomers, i.e., at least about 90% by weight propylene. Such homopolymers may have a melting point of from about 140° C. to about 170° C. Of course, other polyolefins may also be employed in the composition of the present invention. In one embodiment, for example, the polyolefin may be a copolymer of ethylene or propylene with another α-olefin, such as a $C_3$-$C_{20}$ α-olefin or $C_3$-$C_{12}$ α-olefin. Specific examples of suitable α-olefins include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene or propylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

In other embodiments, a polyester may be employed as a matrix polymer. Any of a variety of polyesters may generally be employed, such as aliphatic polyesters, such as polycaprolactone, polyesteramides, polylactic acid (PLA) and its copolymers, polyglycolic acid, polyalkylene carbonates (e.g., polyethylene carbonate), poly-3-hydroxybutyrate (PHB), poly-3-hydroxyvalerate (PHV), poly-3-hydroxybutyrate-co-4-hydroxybutyrate, poly-3-hydroxybutyrate-co-3-hydroxyvalerate copolymers (PHBV), poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate-based aliphatic polymers (e.g., polybutylene succinate, polybutylene succinate adipate, polyethylene succinate, etc.); aliphatic-aromatic copolyesters (e.g., polybutylene adipate terephthalate, polyethylene adipate terephthalate, polyethylene adipate isophthalate, polybutylene adipate isophthalate, etc.); aromatic polyesters (e.g., polyethylene terephthalate, polybutylene terephthalate, etc.); and so forth.

In certain cases, the thermoplastic composition may contain at least one polyester that is rigid in nature, such as polyethylene terephthalate or polylactic acid, and thus has a relatively high glass transition temperature. For example, the glass transition temperature ("$T_g$") may be about 0° C. or more, in some embodiments from about 5° C. to about 120° C., in some embodiments from about 30° C. to about 110° C., and in some embodiments, from about 50° C. to about 100° C. The polyester may also have a melting temperature of from about 140° C. to about 320° C., in some embodiments from about 150° C. to about 300° C., and in some embodiments, from about 160° C. to about 275° C. The melting temperature may be determined using DSC in accordance with ASTM D3417-99. The glass transition temperature may be determined by dynamic mechanical analysis in accordance with ASTM E1640-09. When employed, the rigid polyester typically has a number average molecular weight ("Mn") ranging from about 40,000 to about 180,000 grams per mole, in some embodiments from about 50,000 to about 160,000 grams per mole, and in some embodiments, from about 80,000 to about 120,000 grams per mole. Likewise, the polymer also typically has a weight average molecular weight ("Mw") ranging from about 80,000 to about 250,000 grams per mole, in some embodiments from about 100,000 to about 200,000 grams per mole, and in some embodiments, from about 110,000 to about 160,000 grams per mole. The ratio of the weight average molecular weight to the number average molecular weight ("Mw/Mn"), i.e., the "polydispersity index", is also relatively low. For example, the polydispersity index typically ranges from about 1.0 to about 3.0, in some embodiments from about 1.1 to about 2.0, and in some embodiments, from about 1.2 to about 1.8. The weight and number average molecular weights may be determined by methods known to those skilled in the art. The polyester may also have an intrinsic viscosity of from about 0.2 to about 1.5 deciliters per gram (dL/g), in some embodiments from about 0.4 to about 1.2 dL/g, and in some embodiments, from about 0.5 to about 0.9 dL/g.

Some types of neat polyesters (e.g., polylactic acid) can absorb water from the ambient environment such that it has a moisture content of about 500 to 600 parts per million ("ppm"), or even greater, based on the dry weight of the starting polyester. Moisture content may be determined in a variety of ways as is known in the art, such as in accordance with ASTM D7191-10, such as described below. Because the presence of water during melt processing can hydrolytically degrade the polyester and reduce its molecular weight, it is sometimes desired to dry the polyester prior to blending. In most embodiments, for example, it is desired that the polyester have a moisture content of about 300 parts per million ("ppm") or less, in some embodiments about 200 ppm or less, in some embodiments from about 1 to about 100 ppm prior to blending with the nanoinclusion additive. Drying of the polyester may occur, for instance, at a temperature of from about 50° C. to about 160° C., and in some embodiments, from about 100° C. to about 150° C.

B. Nanoinclusion Additive

As indicated above, a nanoinclusion additive is also employed in the thermoplastic composition that contains at least one polymer. Without intending to be limited by theory, the polymer can be selected so that it is at least partially incompatible with the matrix polymer in the sense that it can be substantially uniformly distributed within the matrix, but in the form of discrete domains. Prior to drawing, the discrete domains may be of a nano-scale size, such as having an average cross-sectional dimension of from about 1 to about 2,500 nanometers, in some embodiments from about 5 to about 2,000 nanometers, in some embodiments from about 10 to about 1,500 nanometers, and in some embodiments from about 20 to about 1,000 nanometers. The domains may have a variety of different shapes, such as elliptical, spherical, cylindrical, plate-like, tubular, etc. In one embodiment, for example, the domains have a substantially elliptical shape. The nanoinclusion additive is typically employed in an amount of from about 0.05 wt. % to about 20 wt. %, in some embodiments from about 0.1 wt. % to about 10 wt. %, and in some embodiments, from about 0.5 wt. % to about 5 wt. %, based on the weight of the continuous phase matrix polymer. The concentration of the nanoinclusion additive in the entire thermoplastic composition may likewise be from about 0.01 wt. % to about 15 wt. %, in some embodiments from about 0.05 wt. % to about 10 wt. %, and in some embodiments, from about 0.3 wt. % to about 6 wt. % of the thermoplastic composition.

The nanoinclusion additive is partially incompatible with the matrix polymer in the sense that it can be substantially uniformly distributed within the matrix, but in the form of discrete domains. Such partial incompatibility can be accomplished in a variety of ways. In certain embodiments, for example, the nanoinclusion additive may be a polymer having a nonpolar component (e.g., siloxane polymer, olefinic polymer, etc.). Such polymers typically have a weight average molecular weight of about 100,000 grams per mole or more, in some embodiments about 200,000 grams per mole or more, and in some embodiments, from about 500,000 grams per mole to about 2,000,000 grams per mole.

In one embodiment, for instance, the nanoinclusion additive may contain a siloxane polymer. The siloxane polymer may have a kinematic viscosity of about $1\times10^5$ centistokes or more, in some embodiments about $5\times10^5$ centistokes or more, in some embodiments about $1\times10^6$ centistokes or more, and in some embodiments, from about $5\times10^6$ centistokes to about $20\times10^6$ centistokes. Any of a variety of nanoinclusion additives may generally be employed in the thermoplastic composition. In certain embodiments, for example, the siloxane polymer may be an "MQ" resin, which is a macromolecular polymer containing $R_3SiO_{1/2}$ and $SiO_{4/2}$ units (the M and Q units, respectively), wherein R is a functional or nonfunctional organic group. Suitable organofunctional groups ("R") may include, for instance, alkyl (e.g., methyl, ethyl, propyl, butyl, etc.), aryl (e.g., phenyl), cycloalkyl (e.g., cyclopentyl), arylenyl, alkenyl, cycloalkenyl (e.g., cyclohexenyl), alkoxy (e.g., methoxy), etc., as well as combinations thereof. Such resins are generally prepared by chemically linking (copolymerizing) MQ resin molecules having a low weight average molecular weight (such as less than 100,000 grams per mole) with polysiloxane linkers. In one particular embodiment, for instance, the resin may be formed by copolymerizing a low molecular weight MQ solid resin (A) with a substantially linear polydiorganosiloxane linker (B), such as described in U.S. Pat. No. 6,072,012 to Juen, et al. The resin (A) may, for instance, have M and Q siloxy units having the following general formula:

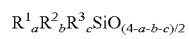

wherein,

R[1] is a hydroxyl group;

$R^2$ is a monovalent hydrocarbon group having at least one unsaturated carbon-carbon bond (i.e., vinyl) that is capable of addition reaction with a silicon-bonded hydrogen atom;

each $R^3$ is independently selected from the group consisting of alkyl, aryl and arylalkyl groups;

a is a number from 0 to 1, and in some embodiments, from 0 to 0.2;

b is number from 0 to 3, and in some embodiments, from 0 to 1.5; and c is a number greater than or equal to 0.

The substantially linear polydiorganosiloxane linker (B) may likewise have the following general formula:

wherein, each $R^4$ is a monovalent group independently selected from the group consisting of alkyl, aryl, and arylalkyl groups;

each $R^5$ is a monovalent group independently selected from the group consisting of hydrogen, hydroxyl, alkoxy, oximo, alkyloximo, and aryloximo groups, wherein at least two $R^5$ groups are typically present in each molecule and bonded to different silicon atoms;

p is 0, 1, 2, or 3;

x ranges from 0 to 200, and in some embodiments, from 0 to 100; and y ranges from 0 to 200, and in some embodiments, from 0 to 100.

In addition to the siloxane polymer, one or more carrier resins may also be employed in the nanoinclusion additive. When employed, the carrier resin typically constitutes from about 20 wt. % to about 80 wt. %, in some embodiments from about 30 wt. % to about 70 wt. %, and in some embodiments, from about 40 wt. % to about 60 wt. % of the nanoinclusion additive. Likewise, siloxane polymers also typically constitute from about 20 wt. % to about 80 wt. %, in some embodiments from about 30 wt. % to about 70 wt. %, and in some embodiments, from about 40 wt. % to about 60 wt. % of the nanoinclusion additive.

Any of a variety of carrier resins may be employed, such as polyolefins (ethylene polymer, propylene polymers, etc.), polyesters (e.g., polyethylene terephthalate, polyester elastomers, etc.), polyamides, etc. In one embodiment, for example, the carrier resin is an ethylene polymer, such as a copolymer of ethylene and an α-olefin, such as described above. The density of the ethylene polymer may vary depending on the type of polymer employed, but generally ranges from about 0.85 to about 0.96 grams per cubic centimeter (g/cm³). Polyethylene "plastomers", for instance, may have a density in the range of from about 0.85 to about 0.91 g/cm³. Likewise, "linear low density polyethylene" (LLDPE) may have a density in the range of from about 0.91 to about 0.940 g/cm³; "low density polyethylene" (LDPE) may have a density in the range of from about 0.910 to about 0.940 g/cm³; and "high density polyethylene" (HDPE) may have density in the range of from about 0.940 to about 0.960 g/cm³, such as determined in accordance with ASTM D792-13. Of course, in other embodiments, the carrier resin may contain a propylene polymer, such as a propylene homopolymer, propylene/α-olefin copolymer, etc., as well as combinations thereof. In one particular embodiment, the polymer is a propylene polymer, such as homopolypropylene or a copolymer of propylene. The propylene polymer may, for instance, be formed from a substantially isotactic polypropylene homopolymer or a copolymer containing equal to or less than about 10 wt. % of other monomer, i.e., at least about 90% by weight propylene. Such homopolymers may have a melting point of from about 160° C. to about 170° C. Commercially available examples of suitable nanoinclusion additive masterbatches that may be employed include, for instance, those available from Dow Corning under the trade designations MB50-001 (propylene homopolymer carrier resin), MB50-313 (LDPE carrier resin), MB50-010 (polyester elastomer carrier resin), and MB50-314 (HDPE carrier resin).

In yet other embodiments, a thermoplastic copolyetherester elastomer may also be employed as a nanoinclusion additive. Without intending to be limited by theory, it is believed that the copolyetherester elastomer is at least partially incompatible with the matrix polymer in the sense that it can be substantially uniformly distributed in the form of discrete domains. Any of a variety of thermoplastic copolyetherester elastomers may generally be employed in the present invention. Typically, such elastomers are segmented block copolymers that have recurring "long chain ester units" and "short chain ester units" joined through ester linkages. The long chain units can be represented by the formula:

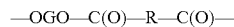

and the short chain ester units are represented by the structure:

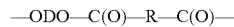

wherein,

G is a divalent group that is derived from one or more high molecular weight alcohols (e.g., polymeric glycol);

R is a hydrocarbon group derived from one or more dicarboxylic acids (e.g., terephthalic acid, isophthalic acid, etc.); and D is a divalent group derived from one or more low molecular weight diols (e.g., 1,4-butane diol, ethylene glycol, etc.).

The "long chain units" are typically formed from the reaction product of a high molecular weight alcohol with a dicarboxylic acid and the "short chain ester units" are typically formed from the reaction of a low molecular weight diol with a dicarboxylic acid. The high molecular weight alcohol may, for instance, have a number average molecular weight of about 400 grams per mole or more, and in some embodiments, from about 600 to about 10,000 grams per mole. Examples of such alcohols include, for instance, polymeric glycols having terminal hydroxy groups, and particularly those derived from 1,2-alkylene oxides containing 2 to about 10 carbon atoms (e.g., ethylene oxide, 1,2-propylene oxide, 1,2-butylene oxide and 1,2-hexylene oxide). In one embodiment, for instance, the high molecular weight alcohol is a random or block copolymer of ethylene oxide and 1,2-propylene oxide. In another embodiment, the high molecular weight alcohol is a poly(oxytetramethylene) glycols derived from tetrahydrofuran. The low molecular weight diols may have a number average molecular weight of less than about 400 grams per mole and in some embodiments, from about 50 to about 300 grams per mole. Examples of suitable diols include, for instance, ethylene glycol, propylene glycol, 1,4-butanediol, 1,6-hexamethylene glycol, dihydroxycyclohexane, cyclohexane dimethanol, resorcinol, hydroquinone, 1,5-dihydroxynaphthalene, bisphenol A and so forth. Equivalent ester forming derivatives of diols, e.g., ethylene oxide or propylene carbonate, may also be employed. Further, if desired, a mixture of high molecular weight alcohols and/or low molecular weight diols may also be employed. Thus, for example, the letter "G" in the formula above may represent the residue of a single long chain glycol or the residue of several different glycols and/or the letter "D" may represent the residue of one or several low molecular weight diols.

The term "dicarboxylic acid" as used herein is intended to include the condensation polymerization equivalents of dicarboxylic acids, i.e., their esters or ester forming derivatives, such as acid chlorides, anhydrides, or other derivatives which behave substantially like dicarboxylic acids in a polymerization reaction with a glycol. The dicarboxylic acids may also be aromatic, aliphatic, and/or aliphatic-aromatic in nature. Particularly suitable aromatic dicarboxylic acids may include, for instance, orthophthalic acid, isophthalic acid, terephthalic acid, bibenzoic acid, etc., as well as esters or ester-forming derivatives thereof. Likewise, suitable aliphatic dicarboxylic acids may include succinic acid, glutaric acid, adipic acid, pimelic acid, suberic acid, azelaic acid, sebacic acid, oxalic acid, fumaric acid, etc., as well as esters or ester-forming derivatives thereof. If desired, a mixture of dicarboxylic acids, such as terephthalic acid and isophthalic acid, may also be employed. Thus, the letter "R" in the formula above may also represent the residue of one or several dicarboxylic acids.

In still other embodiments, the nanoinclusion additive may be an epoxide-functional polyolefin. One example of such a nanoinclusion additive is a polyepoxide that contains, on average, at least two oxirane rings per molecule. Without intending to be limited by theory, it is believed that such polyepoxide molecules can undergo a reaction (e.g., chain extension, side chain branching, grafting, copolymer formation, etc.) with certain components of the composition to improve melt strength without significantly reducing glass transition temperature. In this regard, polyepoxides having a relatively low epoxy functionality may be particularly effective, which may be quantified by its "epoxy equivalent weight." The epoxy equivalent weight reflects the amount of resin that contains one molecule of an epoxy group, and it may be calculated by dividing the number average molecular weight of the modifier by the number of epoxy groups in the molecule. The polyepoxide of the present invention typically has a number average molecular weight from about 7,500 to about 250,000 grams per mole, in some embodiments from about 15,000 to about 150,000 grams per mole, and in some embodiments, from about 20,000 to about 100,000 grams per mole, with a polydispersity index typically ranging from 2.5 to 7. The polyepoxide may contain less than 50, in some embodiments from 5 to 45, and in some embodiments, from 15 to 40 epoxy groups. In turn, the epoxy equivalent weight may be less than about 15,000 grams per mole, in some embodiments from about 200 to about 10,000 grams per mole, and in some embodiments, from about 500 to about 7,000 grams per mole.

The polyepoxide may be a linear or branched, homopolymer or copolymer (e.g., random, graft, block, etc.) containing terminal epoxy groups, skeletal oxirane units, and/or pendent epoxy groups. The monomers employed to form such polyepoxides may vary. In one particular embodiment, for example, the polyepoxide contains at least one epoxy-functional (meth)acrylic monomeric component. As used herein, the term "(meth)acrylic" includes acrylic and methacrylic monomers, as well as salts or esters thereof, such as acrylate and methacrylate monomers. For example, suitable epoxy-functional (meth)acrylic monomers may include, but are not limited to, those containing 1,2-epoxy groups, such as glycidyl acrylate and glycidyl methacrylate. Other suitable epoxy-functional monomers include allyl glycidyl ether, glycidyl ethacrylate, and glycidyl itoconate.

The polyepoxide typically has a relatively high molecular weight, as indicated above, so that it may not only result in chain extension, but also help to achieve the desired blend morphology. The resulting melt flow rate of the polymer is thus typically within a range of from about 10 to about 200 grams per 10 minutes, in some embodiments from about 40 to about 150 grams per 10 minutes, and in some embodiments, from about 60 to about 120 grams per 10 minutes, determined at a load of 2160 grams and at a temperature of 190° C.

The polyepoxide also typically includes at least one linear or branched α-olefin monomer, such as those having from 2 to 20 carbon atoms and preferably from 2 to 8 carbon atoms. Specific examples include ethylene, propylene, 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are ethylene and propylene. Another suitable monomer may include a (meth)acrylic monomer that is not epoxy-functional. Examples of such (meth)acrylic monomers may include methyl acrylate, ethyl acrylate, n-propyl acrylate, i-propyl acrylate, n-butyl acrylate, s-butyl acrylate, i-butyl acrylate, t-butyl acrylate, n-amyl acrylate, i-amyl acrylate, isobornyl acrylate, n-hexyl acrylate, 2-ethylbutyl acrylate, 2-ethylhexyl acrylate, n-octyl acrylate, n-decyl acrylate, methylcyclohexyl acrylate, cyclopentyl acrylate, cyclohexyl acrylate, methyl methacrylate, ethyl methacrylate, 2-hydroxyethyl methacrylate, n-propyl methacrylate, n-butyl methacrylate, i-propyl methacrylate, i-butyl methacrylate, n-amyl methacrylate, n-hexyl methacrylate, i-amyl methacrylate, s-butyl-methacrylate, t-butyl methacrylate, 2-ethylbutyl methacrylate, methylcyclohexyl methacrylate, cinnamyl methacrylate, crotyl methacrylate, cyclohexyl methacrylate, cyclopentyl methacrylate, 2-ethoxyethyl methacrylate, isobornyl methacrylate, etc., as well as combinations thereof.

In one particularly desirable embodiment of the present invention, the polyepoxide is a terpolymer formed from an epoxy-functional (meth)acrylic monomeric component, α-olefin monomeric component, and non-epoxy functional (meth)acrylic monomeric component. For example, the polyepoxide may be poly(ethylene-co-methylacrylate-co-glycidyl methacrylate), which has the following structure:

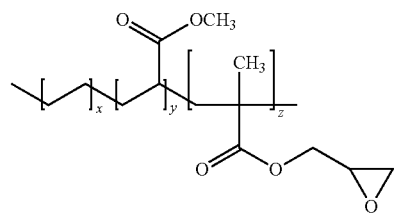

wherein, x, y, and z are 1 or greater.

The epoxy functional monomer may be formed into a polymer using a variety of known techniques. For example, a monomer containing polar functional groups may be grafted onto a polymer backbone to form a graft copolymer. Such grafting techniques are well known in the art and described, for instance, in U.S. Pat. No. 5,179,164. In other embodiments, a monomer containing epoxy functional groups may be copolymerized with a monomer to form a block or random copolymer using known free radical polymerization techniques, such as high pressure reactions, Ziegler-Natta catalyst reaction systems, single site catalyst (e.g., metallocene) reaction systems, etc.

The relative portion of the monomeric component(s) may be selected to achieve a balance between epoxy-reactivity and melt flow rate. More particularly, high epoxy monomer contents can result in good reactivity, but too high of a content may reduce the melt flow rate to such an extent that the polyepoxide adversely impacts the melt strength of the polymer blend. Thus, in most embodiments, the epoxy-functional (meth)acrylic monomer(s) constitute from about 1 wt. % to about 25 wt. %, in some embodiments from about 2 wt. % to about 20 wt. %, and in some embodiments, from about 4 wt. % to about 15 wt. % of the copolymer. The α-olefin monomer(s) may likewise constitute from about 55 wt. % to about 95 wt. %, in some embodiments from about 60 wt. % to about 90 wt. %, and in some embodiments, from about 65 wt. % to about 85 wt. % of the copolymer. When employed, other monomeric components (e.g., non-epoxy functional (meth)acrylic monomers) may constitute from about 5 wt. % to about 35 wt. %, in some embodiments from about 8 wt. % to about 30 wt. %, and in some embodiments, from about 10 wt. % to about 25 wt. % of the copolymer. One specific example of a suitable polyepoxide that may be used in the present invention is commercially available from Arkema under the name LOTADER® AX8950 or AX8900. LOTADER® AX8950, for instance, has a melt flow rate of 70 to 100 g/10 min and has a glycidyl methacrylate monomer content of 7 wt. % to 11 wt. %, a methyl acrylate monomer content of 13 wt. % to 17 wt. %, and an ethylene monomer content of 72 wt. % to 80 wt. %. Another suitable polyepoxide is commercially available from DuPont under the name ELVALOY® PTW, which is a terpolymer of ethylene, butyl acrylate, and glycidyl methacrylate and has a melt flow rate of 12 g/10 min.

In addition to controlling the type and relative content of the monomers used to form the polyepoxide, the overall weight percentage may also be controlled to achieve the desired benefits. For example, if the modification level is too low, the desired increase in melt strength and mechanical properties may not be achieved. The present inventors have also discovered, however, that if the modification level is too high, processing may be restricted due to strong molecular interactions (e.g., crosslinking) and physical network formation by the epoxy functional groups. Thus, the polyepoxide is typically employed in an amount of from about 0.05 wt. % to about 10 wt. %, in some embodiments from about 0.1 wt. % to about 8 wt. %, in some embodiments from about 0.5 wt. % to about 5 wt. %, and in some embodiments, from about 1 wt. % to about 3 wt. %, based on the weight of the polyolefins employed in the composition. The polyepoxide may also constitute from about 0.05 wt. % to about 10 wt. %, in some embodiments from about 0.05 wt. % to about 8 wt. %, in some embodiments from about 0.1 wt. % to about 5 wt. %, and in some embodiments from about 0.5 wt. % to about 3 wt. %, based on the total weight of the composition.

C. Microinclusion Additive

Although not required, the composition of the present invention may also employ a microinclusion additive, such as in an amount of from about 1 wt. % to about 30 wt. %, in some embodiments from about 2 wt. % to about 25 wt. %, and in some embodiments, from about 5 wt. % to about 20 wt. %, based on the weight of the matrix polymer employed in the composition. The concentration of the microinclusion additive in the entire thermoplastic composition may likewise constitute from about 0.1 wt. % to about 30 wt. %, in some embodiments from about 0.5 wt. % to about 25 wt. %, and in some embodiments, from about 1 wt. % to about 20 wt %.

The term "microinclusion additive" generally refers to any material that is capable of being dispersed within the polymer matrix in the form of discrete domains of a micro-scale size. For example, prior to drawing, the domains may have an average cross-sectional dimension of from about 0.1 µm to about 25 µm, in some embodiments from about 0.5 µm to about 20 µm, and in some embodiments from about 1 µm to about 10 µm. When employed, the micro-scale and nano-scale phase domains are able to interact in a unique manner when melt drawn. Namely, it is believed that melt drawing can initiate intensive localized shear zones and/or stress intensity zones (e.g., normal stresses) near the micro-scale discrete phase domains as a result of stress concentrations that arise from the incompatibility of the materials. These shear and/or stress intensity zones cause some initial debonding in the matrix polymer adjacent to the micro-scale domains. Notably, however, the localized shear and/or stress intensity zones created near the nano-scale discrete phase domains may overlap with the micro-scale zones to cause even further debonding to occur in the polymer matrix, thereby creating a substantial number of nanopores adjacent to the nano-scale domains and/or micro-scale domains.

The particular nature of the microinclusion additive is not critical, and may include liquids, semi-solids, or solids (e.g., amorphous, crystalline, or semi-crystalline). In certain embodiments, the microinclusion additive is polymeric in nature and possesses a relatively high molecular weight to help improve the melt strength and stability of the thermoplastic composition. Typically, the microinclusion additive polymer may be generally incompatible with the matrix polymer. In this manner, the additive can better become dispersed as discrete phase domains within a continuous phase of the matrix polymer. The discrete domains are capable of absorbing energy that arises from an external force, which increases the overall toughness and strength of the resulting fibers. The domains may have a variety of different shapes, such as elliptical, spherical, cylindrical, plate-like, tubular, etc. In one embodiment, for example, the domains have a substantially elliptical shape. The physical dimension of an individual domain is typically small enough to minimize the propagation of cracks through the material upon the application of an external stress, but large enough to initiate microscopic plastic deformation and allow for shear zones at and around particle inclusions.

As noted above, the microinclusion additive may also have a certain melt flow rate (or viscosity) to ensure that the discrete domains and resulting pores can be adequately maintained. For example, the ratio of the melt flow rate of the microinclusion additive to the melt flow rate of the matrix polymer is typically from about 0.2 to about 8, in some embodiments from about 0.5 to about 6, and in some embodiments, from about 1 to about 5. The microinclusion additive may, for example, have a melt flow rate of from about 0.1 to about 250 grams per 10 minutes, in some embodiments from about 0.5 to about 200 grams per 10 minutes, and in some embodiments, from about 5 to about 150 grams per 10 minutes, determined at a load of 2160 grams and at a temperature at least about 40° C. above its melting temperature (e.g., 120° C. to 180° C.).

While a wide variety of microinclusion additives may be employed that have the properties identified above, particularly suitable examples of such additives may include synthetic polymers, such as polyolefins (e.g., polyethylene, polypropylene, polybutylene, etc.); styrenic copolymers (e.g., styrene-butadiene-styrene, styrene-isoprene-styrene, styrene-ethylene-propylene-styrene, styrene-ethylene-butadiene-styrene, etc.); polytetrafluoroethylenes; polyesters (e.g., recycled polyester, polyethylene terephthalate, etc.); polyvinyl acetates (e.g., poly(ethylene vinyl acetate), polyvinyl chloride acetate, etc.); polyvinyl alcohols (e.g., polyvinyl alcohol, poly(ethylene vinyl alcohol), etc.); polyvinyl butyrals; acrylic resins (e.g., polyacrylate, polymethylacrylate, polymethylmethacrylate, etc.); polyamides (e.g., nylon); polyvinyl chlorides; polyvinylidene chlorides; polystyrenes; polyurethanes; etc. Suitable polyolefins may, for instance, include ethylene polymers (e.g., LDPE, HDPE, LLDPE, etc.), propylene homopolymers (e.g., syndiotactic, atactic, isotactic, etc.), propylene copolymers, and so forth.

In certain embodiments, the microinclusion additive may also serve as the carrier resin for the nanoinclusion additive, as discussed above. In such embodiments, it may be particularly suitable to employ a polyolefin for the microinclusion additive.

D. Other Components

Other suitable materials that may also be used in the thermoplastic composition, such as lubricants, compatibilizers, catalysts, antioxidants, stabilizers, surfactants, waxes, solid solvents, nucleating agents, particulates, nanofillers, and other materials added to enhance the processability and mechanical properties of the thermoplastic composition. Nevertheless, one beneficial aspect of the present invention is that good properties may be provided without the need for various conventional additives, such as blowing agents (e.g., chlorofluorocarbons, hydrochlorofluorocarbons, hydrocarbons, carbon dioxide, supercritical carbon dioxide, nitrogen, etc.), pore-initiating fillers (e.g., calcium carbonate), and hydrophobic interphase modifiers (e.g., polyether polyol). In fact, the thermoplastic composition may be generally free of blowing agents, pore-initiating fillers, and/or interphase modifiers. For example, such blowing agents, fillers, and/or interphase modifiers may be present in an amount of no more than about 1 wt. %, in some embodiments no more than about 0.5 wt. %, and in some embodiments, from about 0.001 wt. % to about 0.2 wt. % of the thermoplastic composition. Further, due to its stress whitening properties, as described in more detail below, the resulting composition may achieve an opaque color (e.g., white) without the need for conventional pigments, such as titanium dioxide. In certain embodiments, for example, pigments may be present in an amount of no more than about 1 wt. %, in some embodiments no more than about 0.5 wt. %, and in some embodiments, from about 0.001 wt. % to about 0.2 wt. % of the thermoplastic composition.

II. Fibers

As used herein, the term "fiber" generally refers to an elongated extrudate formed by passing a polymer through a forming orifice, such as a die. Unless noted otherwise, the term "fiber" includes both discontinuous fibers having a definite length and substantially continuous filaments. Substantially filaments may, for instance, have a length much greater than their diameter, such as a length to diameter ratio ("aspect ratio") greater than about 15,000 to 1, and in some cases, greater than about 50,000 to 1. In one embodiment, the fibers may have an average diameter of from about 1 to about 100 micrometers, in some embodiments from about 2 to about 30 micrometers, and in some embodiments, from about 4 to about 15 micrometers.

Fibers may generally have any desired configuration, including monocomponent and multicomponent (e.g., sheath-core configuration, side-by-side configuration, segmented pie configuration, island-in-the-sea configuration, and so forth). Hollow fibers (monocomponent and/or multicomponent) may also be employed, such as described in U.S. Pat. No. 6,642,429 to Carter, et al. In some embodiments, the fibers may contain one or more additional polymers as a component (e.g., bicomponent) or constituent (e.g., biconstituent) to further enhance strength, processibility, and/or other properties. For instance, the thermoplastic composition may form a core component of a sheath/core bicomponent fiber, while an additional polymer may form the sheath component, or vice versa. The additional polymer may be any polymer desired, such as polyesters, e.g., polylactic acid, polyethylene terephthalate, etc.; polyolefins, e.g., polyethylene, polypropylene, polybutylene, and so forth; polytetrafluoroethylene; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; and polyurethanes.

Due to the presence of the porous network, the resulting fibers are not generally brittle and thus can deform upon the application of strain, rather than fracture. In this regard, the fibers are capable of exhibiting good "peak elongation properties, i.e., the percent elongation at its peak load. For example, the fibers may exhibit a peak elongation of about 50% or more, in some embodiments about 100% or more, and in some embodiments, from about 80% to about 500%, such as determined in accordance with ASTM D638-14 at 23° C. Such elongations may be achieved for materials having a wide variety of fiber diameters, such as those ranging from about 0.1 to about 50 micrometers, in some embodiments from about 1 to about 40 micrometers, in some embodiments from about 2 to about 25 micrometers, and in some embodiments, from about 5 to about 15 micrometers. While possessing the ability to extend under strain, the fibers can also be relatively strong. For example, the fibers may exhibit a peak tensile stress of from about 20 to about 600 Megapascals ("MPa"), in some embodiments from about 25 to about 450 MPa, and in some embodiments, from about 30 to about 350 MPa, such as determined in accordance with ASTM D638-14 at 23° C. The fibers may also have a tenacity of from about 0.75 to about 10 grams-force ("$g_f$") per denier, in some embodiments from about 1 to about 8 $g_f$ per denier, and in some embodiments, from about 1.5 to about 6 $g_f$ per denier. The denier of the fibers may vary depending on the desired application. Typically, the fibers are formed to have a denier per filament (i.e., the unit of linear density equal to the mass in grams per 9000 meters of fiber) of less than about 30, in some embodiments less than about 15, and in some embodiments, from about 0.5 to about 10.

Although by no means required, the fibers may be converted into a different form before being employed in a final article or product. For instance, the fibers may be subsequently formed into a nonwoven web structure by randomly depositing the fibers onto a forming surface (optionally with the aid of a vacuum) and then bonding the resulting web using any known technique. The nonwoven web may be formed before or after the fibers are drawn. In certain embodiments, for instance, it may be desired to form a nonwoven web from a plurality of fibers, and thereafter draw the fibers by stretching the nonwoven web to the extent desired to form the porous network. In an alternative embodiment, an endless forming surface may simply be positioned below a fiber aspiration unit that draws the fibers to the desired extent before the web is formed.

Once formed, the nonwoven web may then be bonded using any conventional technique, such as with an adhesive or autogenously (e.g., fusion and/or self-adhesion of the fibers without an applied external adhesive). Autogenous bonding, for instance, may be achieved through contact of the fibers while they are semi-molten or tacky, or simply by blending a tackifying resin and/or solvent with the polymer used to form the fibers. Suitable autogenous bonding techniques may include ultrasonic bonding, thermal bonding, through-air bonding, calendar bonding, and so forth. For example, the web may be further bonded or embossed with a pattern by a thermo-mechanical process in which the web is passed between a heated smooth anvil roll and a heated pattern roll. The pattern roll may have any raised pattern which provides the desired web properties or appearance. Desirably, the pattern roll defines a raised pattern which defines a plurality of bond locations which define a bond area between about 2% and 30% of the total area of the roll. Exemplary bond patterns include, for instance, those described in U.S. Pat. No. 3,855,046 to Hansen et al., U.S. Pat. No. 5,620,779 to Levy et al., U.S. Pat. No. 5,962,112 to Haynes et al., U.S. Pat. No. 6,093,665 to Sayovitz et al., as well as U.S. Design Pat. Nos. 428,267 to Romano et al.; 390,708 to Brown; 418,305 to Zander, et al.; 384,508 to Zander, et al.; 384,819 to Zander, et al.; 358,035 to Zander, et al.; and 315,990 to Blenke, et al. The pressure between the rolls may be from about 5 to about 2000 pounds per lineal inch. The pressure between the rolls and the temperature of the rolls is balanced to obtain desired web properties or appearance while maintaining cloth like properties. As is well known to those skilled in the art, the temperature and pressure required may vary depending upon many factors including but not limited to, pattern bond area, polymer properties, fiber properties and nonwoven properties.

In addition to spunbond webs, a variety of other nonwoven webs may also be formed from the thermoplastic composition in accordance with the present invention, such as meltblown webs, bonded carded webs, wet-laid webs, airlaid webs, coform webs, hydraulically entangled webs, etc. For example, the thermoplastic composition may be extruded through a plurality of fine die capillaries into a converging high velocity gas (e.g., air) streams that attenuate the fibers to reduce their diameter. Thereafter, the meltblown fibers are carried by the high velocity gas stream and are deposited on a collecting surface to form a web of randomly dispersed meltblown fibers. Alternatively, the polymer may be formed into a carded web by placing bales of fibers formed from the thermoplastic composition into a picker that separates the fibers. Next, the fibers are sent through a combing or carding unit that further breaks apart and aligns the fibers in the machine direction so as to form a machine direction-oriented fibrous nonwoven web. Once formed, the nonwoven web is typically stabilized by one or more known bonding techniques as described above to form a bonded carded web. Composites and/or laminates may also be formed from the fibers.

III. Articles

Due to its unique and beneficial properties, the fibers of the present invention are well suited for use in a variety of different types of articles, such as an absorbent article, packaging film, barrier film, medical product (e.g., gown, surgical drape, facemask, head covering, surgical cap, shoe covering, sterilization wrap, warming blanket, heating pad, etc.), and so forth. For example, the fibers may be incorporated into an "absorbent article" that is capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, mitt wipe, and so forth; medical absorbent articles, such as garments, fenestration materials, underpads, bedpads, bandages, absorbent drapes, and medical wipes; food service wipers; clothing articles; pouches, and so forth. Materials and processes suitable for forming such articles are well known to those skilled in the art. Absorbent articles, for instance, typically include a substantially liquid-impermeable layer (e.g., outer cover), a liquid-permeable layer (e.g., bodyside liner, surge layer, etc.), and an absorbent core. In one embodiment, for example, the fibers may be in the form of a nonwoven web and used to form an outer cover of an absorbent article. If desired, the nonwoven web may be laminated to a liquid-impermeable film that is either vapor-permeable or vapor-impermeable.

Absorbent articles, for instance, generally include an absorbent member (e.g., core layer, surge layer, transfer delay layer, wrapsheet, ventilation layer, etc.) positioned between a backsheet and a topsheet. The absorbent article may also contain other components as is known in the art, such as side panels, containment flaps, ears, waist or leg bands, etc. Generally speaking, the fibers of the present invention may be employed in any layer or component of the absorbent article, such as the topsheet, backsheet, and/or absorbent member. When employed in certain layers or components (e.g., backsheet), it may be desirable to laminate the fibers (e.g., in the form of a nonwoven web) to another layer (e.g., a film).

In this regard, various exemplary embodiments of the absorbent article will be described. Referring to FIG. 1, for instance, one particular embodiment of an absorbent article 201 is shown in the form of a diaper. However, as noted above, the invention may be embodied in other types of absorbent articles, such as incontinence articles, sanitary napkins, diaper pants, feminine napkins, training pants, and so forth. In the illustrated embodiment, the absorbent article 201 is shown as having an hourglass shape in an unfastened configuration. However, other shapes may of course be utilized, such as a generally rectangular shape, T-shape, or I-shape. As shown, the absorbent article 201 includes a chassis 202 formed by various components, including a backsheet 217, topsheet 205, and absorbent member that includes an absorbent core layer 203 and surge layer 207. It should be understood, however, that other layers may also be used in the present invention. Likewise, one or more of the layers referred to in FIG. 1 may also be eliminated in certain embodiments of the present invention.

As indicated above, the backsheet 217 may contain the fibers of the present invention. If desired, the nonwoven web may be positioned so that it defines a garment-facing surface 333 of the absorbent article 201. The absorbent article 201 also includes a topsheet 205. The topsheet 205 is generally designed to contact the body of the user and is liquid-permeable. For example, the topsheet 205 may define a body-facing surface 218, which is typically compliant, soft feeling, and non-irritating to the wearers skin. If desired, the topsheet 205 may contain the fibers (e.g., nonwoven web) of the present invention. For example, the nonwoven web may be positioned so that it defines the body-facing surface 218 if so desired. The topsheet may surround the absorbent core layer 203 so that it completely encases the absorbent article. Alternatively, the topsheet 205 and the backsheet 217 may extend beyond the absorbent member and be peripherally joined together, either entirely or partially, using known techniques, such as by adhesive bonding, ultrasonic bonding, etc. As indicated above, the topsheet 205 may include the fibers (e.g., nonwoven web) of the present invention. The topsheet 205 may also include a conventional a nonwoven web (e.g., spunbond web, meltblown web, or bonded carded web). Other exemplary topsheet constructions that contain a nonwoven web are described in U.S. Pat. Nos. 5,192,606; 5,702,377; 5,931,823; 6,060,638; and 6,150,002, as well as U.S. Patent Application Publication Nos. 2004/0102750, 2005/0054255, and 2005/0059941. The topsheet 205 may also contain a plurality of apertures formed therethrough to permit body fluid to pass more readily into the absorbent core layer 203. The apertures may be randomly or uniformly arranged throughout the topsheet 205, or they may be located only in the narrow longitudinal band or strip arranged along the longitudinal axis of the absorbent article. The apertures permit rapid penetration of body fluid down into the absorbent member. The size, shape, diameter and number of apertures may be varied to suit one's particular needs.

The absorbent article also contains an absorbent member positioned between the topsheet and the backsheet. The absorbent member may be formed from a single absorbent layer or a composite containing separate and distinct absorbent layer. It should be understood, however, that any number of absorbent layers may be utilized in the present invention. In FIG. 1, for instance, the absorbent member contains an absorbent core layer 203 and a surge layer 207 that helps to decelerate and diffuse surges or gushes of liquid that may be rapidly introduced into the absorbent core layer 203. Desirably, the surge layer 207 rapidly accepts and temporarily holds the liquid prior to releasing it into the storage or retention portions of the absorbent core layer 203. In the illustrated embodiment, for example, the surge layer 207 is interposed between an inwardly facing surface 216 of the topsheet 205 and the absorbent core layer 203. Alternatively, the surge layer 207 may be located on the outwardly facing surface 218 of the topsheet 205. The surge layer 207 is typically constructed from highly liquid-permeable materials. Suitable materials may include porous woven materials, porous nonwoven materials, and apertured films. In one embodiment, the surge layer 207 may contain the fibers of the present invention. Other examples of suitable surge layers are described in U.S. Pat. No. 5,486,166 to Ellis, et al. and U.S. Pat. No. 5,490,846 to Ellis, et al.

If desired, the absorbent member may also contain a transfer delay layer positioned vertically below the surge layer. The transfer delay layer may contain a material that is less hydrophilic than the other absorbent layers, and may generally be characterized as being substantially hydrophobic. For example, the transfer delay layer may contains the fibers (e.g., nonwoven web) of the present invention. The fibers may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay layer are described in U.S. Pat. No. 4,798,603 to Meyer, et al. and U.S. Pat. No. 5,248,309 to Serbiak, et al. To adjust the performance of the invention, the transfer delay layer may also be treated with a selected amount of surfactant to increase its initial wettability.

The transfer delay layer may generally have any size, such as a length of about 150 mm to about 300 mm. Typically, the length of the transfer delay layer is approximately equal to the length of the absorbent article. The transfer delay layer may also be equal in width to the surge layer, but is typically wider. For example, the width of the transfer delay layer may be from between about 50 mm to about 75 mm, and particularly about 48 mm. The transfer delay layer typically has a basis weight less than that of the other absorbent members. For example, the basis weight of the transfer delay layer is typically less than about 150 grams per square meter (gsm), and in some embodiments, between about 10 gsm to about 100 gsm. If desired, the transfer delay layer may contain the fibers (e.g., nonwoven web) of the present invention.

Besides the above-mentioned components, the absorbent article 201 may also contain various other components as is known in the art. For example, the absorbent article 201 may also contain a substantially hydrophilic wrapsheet (not illustrated) that helps maintain the integrity of the fibrous structure of the absorbent core layer 203. The wrapsheet is typically placed about the absorbent core layer 203 over at least the two major facing surfaces thereof, and composed of an absorbent cellulosic material, such as creped wadding or a high wet-strength tissue. The wrapsheet may be configured to provide a wicking layer that helps to rapidly distribute liquid over the mass of absorbent fibers of the absorbent core layer 203. The wrapsheet material on one side of the absorbent fibrous mass may be bonded to the wrapsheet located on the opposite side of the fibrous mass to effectively entrap the absorbent core layer 203. Furthermore, the absorbent article 201 may also include a ventilation layer (not shown) that is positioned between the absorbent core layer 203 and the backsheet 217. When utilized, the ventilation layer may help insulate the backsheet 217 from the absorbent core layer 203, thereby reducing dampness in the backsheet 217. Examples of such ventilation layers may include a nonwoven web laminated to a breathable film, such as described in U.S. Pat. No. 6,663,611 to Blaney, et al. If desired, the wrapsheet and/or ventilation layer may contain the fibers of the present invention.

In some embodiments, the absorbent article 201 may also include a pair of ears (not shown) that extend from the side edges 232 of the absorbent article 201 into one of the waist regions. The ears may be integrally formed with a selected diaper component. For example, the ears may be integrally formed with the backsheet 217 or from the material employed to provide the top surface, which may include the fibers of the present invention if so desired. In alternative configurations, the ears may be provided by members connected and assembled to the backsheet 217, the top surface, between the backsheet 217 and top surface, or in various other configurations. As noted above, the ears may contain the fibers of the present invention if so desired.

As representatively illustrated in FIG. 1, the absorbent article 201 may also include a pair of containment flaps 212 that are configured to provide a barrier and to contain the lateral flow of body exudates. The containment flaps 212 may be located along the laterally opposed side edges 232 of the topsheet 205 adjacent the side edges of the absorbent core layer 203. The containment flaps 212 may extend longitudinally along the entire length of the absorbent core layer 203, or may only extend partially along the length of the absorbent core layer 203. When the containment flaps 212 are shorter in length than the absorbent core layer 203, they may be selectively positioned anywhere along the side edges 232 of absorbent article 201 in a crotch region 210. In one embodiment, the containment flaps 212 extend along the entire length of the absorbent core layer 203 to better contain the body exudates. Such containment flaps 212 are generally well known to those skilled in the art. For example, suitable constructions and arrangements for the containment flaps 212 are described in U.S. Pat. No. 4,704,116 to Enloe. If desired, the containment flaps may contain the fibers of the present invention.

The absorbent article 201 may include various elastic or stretchable materials, such as a pair of leg elastic members 206 affixed to the side edges 232 to further prevent leakage of body exudates and to support the absorbent core layer 203. In addition, a pair of waist elastic members 208 may be affixed to longitudinally opposed waist edges 215 of the absorbent article 201. The leg elastic members 206 and the waist elastic members 208 are generally adapted to closely fit about the legs and waist of the wearer in use to maintain a positive, contacting relationship with the wearer and to effectively reduce or eliminate the leakage of body exudates from the absorbent article 201. The absorbent article 201 may also include one or more fasteners 230. For example, two flexible fasteners 130 are illustrated in FIG. 1 on opposite side edges of waist regions to create a waist opening and a pair of leg openings about the wearer. The shape of the fasteners 230 may generally vary, but may include, for instance, generally rectangular shapes, square shapes, circular shapes, triangular shapes, oval shapes, linear shapes, and so forth. The fasteners may include, for instance, a hook material. In one particular embodiment, each fastener 230 includes a separate piece of hook material affixed to the inside surface of a flexible backing. The elastic members (e.g., leg, waist, etc.) and/or fasteners may contain the fibers of the present invention if desired.

The various regions and/or components of the absorbent article 201 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the backsheet 217 and topsheet 205 are assembled to each other and to the absorbent core layer 203 using an adhesive. Alternatively, the absorbent core layer 203 may be connected to the backsheet 217 using conventional fasteners, such as buttons, hook and loop type fasteners, adhesive tape fasteners, and so forth. Similarly, other diaper components, such as the leg elastic members 206, waist elastic members 208 and fasteners 230, may also be assembled into the absorbent article 201 using any attachment mechanism.

Although various configurations of a diaper have been described above, it should be understood that other diaper and absorbent article configurations are also included within the scope of the present invention. In addition, the present invention is by no means limited to diapers. In fact, any other absorbent article may be formed in accordance with the present invention, including, but not limited to, other personal care absorbent articles, such as training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth.

The fibers may also be employed in a wide variety of other types of articles. Non-limiting examples include, for instance, insulation materials for refrigeration units (e.g., refrigerators, freezers, vending machines, etc.); automotive components (e.g., front and rear seats, headrests, armrests, door panels, rear shelves/package trays, steering wheels and interior trim, dashboards, etc.); building panels and sections (e.g., roofs, wall cavities, under floors, etc.); apparel (e.g., coats, shirts, pants, gloves, aprons, coveralls, shoes, boots, headware, sock liners, etc.); furniture and bedding (e.g., sleeping bags, comforters, etc.); fluid storage/transfer systems (e.g., pipes or tankers for liquid/gas hydrocarbons, liquid nitrogen, oxygen, hydrogen, or crude oil); extreme environments (e.g., underwater or space); food and beverage products (e.g., cups, cup holders, plates, etc.); containers and bottles; industrial fabrics; insulation fabrics; and so forth. The fibers may also be used in a "garment", which is generally meant to include any article that is shaped to fit over a portion of a body. Examples of such articles include, without limitation, clothing (e.g., shirts, pants, jeans, slacks, skirts, coats, activewear, athletic, aerobic, and exercise apparel, swimwear, cycling jerseys or shorts, swimsuit/bathing suit, race suit, wetsuit, bodysuit, etc.), footwear (e.g., shoes, socks, boots, etc.), protective apparel (e.g., firefighter's coat), clothing accessories (e.g., belts, bra straps, side panels, gloves, hosiery, leggings, orthopedic braces, etc.), undergarments (e.g., underwear, t-shirts, etc.), compression garments, draped garments (e.g., kilts loincloths, togas, ponchos, cloaks, shawls, etc.), and so forth.

The present invention may be better understood with reference to the following examples.

Test Methods

Melt Flow Rate:

The melt flow rate ("MFR") is the weight of a polymer (in grams) forced through an extrusion rheometer orifice (0.0825-inch diameter) when subjected to a load of 2160 grams in 10 minutes, such as at 190° C., 210° C., 230° C., or 260° C. Unless otherwise indicated, melt flow rate is measured in accordance with ASTM Test Method D1238-13 with a Tinius Olsen Extrusion Plastometer.

Thermal Properties:

The glass transition temperature ($T_g$) may be determined by dynamic mechanical analysis (DMA) in accordance with ASTM E1640-13. A Q800 instrument from TA Instruments may be used. The experimental runs may be executed in tension/tension geometry, in a temperature sweep mode in the range from −120° C. to 150° C. with a heating rate of 3° C./min. The strain amplitude frequency may be kept constant (2 Hz) during the test. Three (3) independent samples may be tested to get an average glass transition temperature, which is defined by the peak value of the tan δ curve, wherein tan δ is defined as the ratio of the loss modulus to the storage modulus (tan δ=E"/E').

The melting temperature may be determined by differential scanning calorimetry (DSC). The differential scanning calorimeter may be a DSC Q100 Differential Scanning Calorimeter, which may be outfitted with a liquid nitrogen cooling accessory and with a UNIVERSAL ANALYSIS 2000 (version 4.6.6) analysis software program, both of which are available from T.A. Instruments Inc. of New Castle, Del. To avoid directly handling the samples, tweezers or other tools may be used. The samples may be placed into an aluminum pan and weighed to an accuracy of 0.01 milligram on an analytical balance. A lid may be crimped over the material sample onto the pan. Typically, the resin pellets may be placed directly in the weighing pan.

The differential scanning calorimeter may be calibrated using an indium metal standard and a baseline correction may be performed, as described in the operating manual for the differential scanning calorimeter. A material sample may be placed into the test chamber of the differential scanning calorimeter for testing, and an empty pan may be used as a reference. All testing may be run with a 55-cubic centimeter per minute nitrogen (industrial grade) purge on the test chamber. For resin pellet samples, the heating and cooling program is a 2-cycle test that began with an equilibration of the chamber to −30° C., followed by a first heating period at a heating rate of 10° C. per minute to a test temperature (e.g., 200° C. or 300° C.), followed by equilibration of the sample at the test temperature for 3 minutes, followed by a first cooling period at a cooling rate of 10° C. per minute to a temperature of −30° C., followed by equilibration of the sample at −30° C. for 3 minutes, and then a second heating period at a heating rate of 10° C. per minute to the test temperature. For fiber samples, the heating and cooling program may be a 1-cycle test that begins with an equilibration of the chamber to −25° C., followed by a heating period at a heating rate of 10° C. per minute to the test temperature, followed by equilibration of the sample at the test temperature for 3 minutes, and then a cooling period at a cooling rate of 10° C. per minute to a temperature of −30° C. All testing may be run with a 55-cubic centimeter per minute nitrogen (industrial grade) purge on the test chamber.

The results may be evaluated using the UNIVERSAL ANALYSIS 2000 analysis software program, which identifies and quantifies the glass transition temperature ($T_g$) of inflection, the endothermic and exothermic peaks, and the areas under the peaks on the DSC plots. The glass transition temperature may be identified as the region on the plot-line where a distinct change in slope occurred, and the melting temperature may be determined using an automatic inflection calculation.

Fiber Tensile Properties:

Fiber tensile properties may be determined in accordance with ASTM D638-14 at 23° C. For instance, individual fiber specimens may initially be shortened (e.g., cut with scissors) to 38 millimeters in length, and placed separately on a black velvet cloth. 10 to 15 fiber specimens may be collected in this manner. The fiber specimens may then be mounted in a substantially straight condition on a rectangular paper frame having external dimension of 51 millimeters×51 millimeters and internal dimension of 25 millimeters×25 millimeters. The ends of each fiber specimen may be operatively attached to the frame by carefully securing the fiber ends to the sides of the frame with adhesive tape. Each fiber specimen may be measured for its external, relatively shorter, cross-fiber dimension employing a conventional laboratory microscope, which may be properly calibrated and set at 40× magnification. This cross-fiber dimension may be recorded as the diameter of the individual fiber specimen. The frame helps to mount the ends of the sample fiber specimens in the upper and lower grips of a constant rate of extension type tensile tester in a manner that avoids excessive damage to the fiber specimens.

A constant rate of extension type of tensile tester and an appropriate load cell may be employed for the testing. The load cell may be chosen (e.g., 10N) so that the test value falls within 10-90% of the full scale load. The tensile tester (i.e., MTS SYNERGY 200) and load cell may be obtained from MTS Systems Corporation of Eden Prairie, Mich. The fiber specimens in the frame assembly may then be mounted between the grips of the tensile tester such that the ends of the fibers may be operatively held by the grips of the tensile tester. Then, the sides of the paper frame that extend parallel to the fiber length may be cut or otherwise separated so that the tensile tester applies the test force only to the fibers. The fibers may be subjected to a pull test at a pull rate and grip speed of 12 inches per minute. The resulting data may be analyzed using a TESTWORKS 4 software program from the MTS Corporation with the following test settings:

| Calculation Inputs | | Test Inputs | |
|---|---|---|---|
| Break mark drop | 50% | Break sensitivity | 90% |
| Break marker elongation | 0.1 in | Break threshold | 10 $g_f$ |
| Nominal gage length | 1 in | Data Acq. Rate | 10 Hz |
| Slack pre-load | 1 $lb_f$ | Denier length | 9000 m |
| Slope segment length | 20% | Density | 1.4 g/cm³ (PET) or 1.25 (PLA) |
| Yield offset | 0.20% | Initial speed | 12 in/min |
| Yield segment length | 2% | Secondary speed | 2 in/min |

The tenacity values may be expressed in terms of gram-force per denier. Peak elongation (% strain at break) and peak stress may also be measured.

Expansion Ratio, Density, and Percent Pore Volume:

To determine expansion ratio, density, and percent pore volume, the width ($W_i$) and thickness ($T_i$) of the specimen may be initially measured prior to drawing. The length ($L_i$) before drawing may also be determined by measuring the distance between two markings on a surface of the specimen. Thereafter, the specimen may be drawn to initiate voiding. The width ($W_f$), thickness ($T_f$), and length ($L_f$) of the specimen may then be measured to the nearest 0.01 mm utilizing Digimatic Caliper (Mitutoyo Corporation). The volume ($V_i$) before drawing may be calculated by $W_i \times T_i \times L_i = V_i$. The volume ($V_f$) after drawing may also be calculated by $W_f \times T_f \times L_f = V_f$. The expansion ratio ($\phi$) may be calculated by $\phi = V_f/V_i$; the density ($P_f$) may be calculated by: $P_f = P_i/\phi$, where $P_i$ is density of precursor material; and the percent pore volume (% $V_v$) may be calculated by: % $V_v = (1 - 1/\phi) \times 100$.

For fibers, the void content may also be measured by suspension in calibrated density solutions. For example, density solutions can be produced by mixing sodium bromide (Sigma-Aldrich) with deionized water to create solutions with densities ranging from 1.0 gram per cubic centimeter (g/cc) to 1.385 g/cc. The solution density may be verified using calibrated hygrometers obtained from VWR.

Example 1

A blend of 93 wt. % semi-crystalline polyethylene terephthalate (Eastlon PET CFF-A17 from Far Eastern New Century Corporation) and 7 wt. % polyester-polyether copolymer (Hytrel RS 40FS NC010, DuPont). Both the polyester and the polyester-polyether copolymer were dry blended and then fed into a twin screw extruder). The polymers were fed into a co-rotating, twin-screw extruder (ZSK-30, diameter of 30 mm, length of 1328 millimeters) for compounding that was manufactured by Werner and Pfleiderer Corporation of Ramsey, N.J. The extruder possessed 14 zones, numbered consecutively 1-14 from the feed hopper to the die. The first barrel zone #1 received the resins via gravimetric feeder at a total throughput of 20 pounds per hour. The die used to extrude the resin had 3 die openings (6 millimeters in diameter) that were separated by 4 millimeters. Upon formation, the extruded resin was cooled on a fan-cooled conveyor belt and formed into pellets by a Conair pelletizer. The extruder screw speed was 200 revolutions per minute ("rpm"). The pellets were dried via a desiccant drying at 140° C. for 12 hours.

Example 2

The resin blend from EXAMPLE 1 was spun into a monocomponent fiber bundle containing 144 filaments group into two 72 fiber tows through a spinneret having a diameter of 0.3 mm. The extrusion temperature was 300° C. and the throughput of 0.96 ghm. The tow was drawn at a speed of 2500 mpm resulting in a total fiber bundle denier of 261 g per 9000 meters.

Example 3

A fiber bundle was formed as in EXAMPLE 2, except that the take up speed was 3000 meters per minute resulting in a denier of 212 g per 9000 meters.

Example 4

A fiber bundle was formed as in EXAMPLE 2, except that the take up speed was 4000 meters per minute resulting in a denier of 126 g per 9000 meters.

Example 5

A fiber bundle was formed as in EXAMPLE 2, except that the take up speed was 5000 meters per minute resulting in a denier of 133 g per 9000 meters.

Example 6

Monocomponent fibers were formed from a 100 wt. % semi-crystalline polyethylene terephthalate (Eastlon PET CFF-A17 from Far Eastern New Century Corporation) into a bundle containing 144 filaments group into two 72 fiber tows through a spinneret having a diameter of 0.3 mm. The extrusion temperature was 300° C. and the throughput of 0.96 ghm. The tow was drawn at a speed of 2500 mpm resulting in a total fiber bundle denier of 267 g per 9000 meters.

Example 7

A fiber bundle was formed as in EXAMPLE 6, except that the take up speed was 3500 meters per minute resulting in a denier of 192 g per 9000 meters.

Example 8

A fiber bundle was formed as in EXAMPLE 6, except that the take up speed was 4000 meters per minute resulting in a denier of 172 g per 9000 meters.

Example 9

A fiber bundle was formed as in EXAMPLE 6, except that the take up speed was 4500 meters per minute resulting in a denier of 152 g per denier.

Example 10

A fiber bundle was formed as in EXAMPLE 6, except that the take up speed was 5000 meters per minute resulting in a denier of 139 g per 9000 meters.

Example 11

A blend of 93 wt. % semi-crystalline polyethylene terephthalate (Eastlon PET CFF-A17 from Far Eastern New Century Corporation) and 7 wt. % linear low density polyethylene (Aspun 6835A-LLDPE Dow Chemical) was used to comprise the core of a bicomponent fibers with a sheath of 100% semi-crystalline polyethylene terephthalate (Eastlon PET CFF-A17 from Far Eastern New Century Corporation) at a ratio of 70% core and 30% sheath. The bicomponent fiber bundle containing 144 filaments group into two 72 fiber tows through a spinneret having a diameter of 0.3 mm. The extrusion temperature was 290° C. and the throughput of 0.96 ghm. The tow was drawn at a speed of 3000 mpm.

Example 12

A fiber bundle was formed as in EXAMPLE 11, except that the take up speed was 4000 meters per minute.

Example 13

A fiber bundle was formed as in EXAMPLE 11, except that the take up speed was 5000 meters per minute.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for forming a fiber, the method comprising:
   extruding a matrix polymer and a nanoinclusion additive to form a thermoplastic composition in which the nanoinclusion additive is dispersed within a continuous phase of the matrix polymer, wherein the nanoinclusion additive contains a copolyetherester elastomer; and
   thereafter, passing the extruded thermoplastic composition through a spinneret to form a fiber having a porous network containing a plurality of nanopores, wherein the average percent volume occupied by the nanopores within a given unit volume of the fiber is from about 3% to about 15% per $cm^3$.

2. The method of claim 1, wherein the spinneret has a length-to-diameter ratio of about 6:1 or less.

3. The method of claim 1, wherein the ratio of the melt flow rate of the matrix polymer to the melt flow rate of the nanoinclusion additive is about 2:1 or more.

4. The method of claim 1, wherein the nanoinclusion additive has a melt flow rate of from about 0.1 to about 50 grams per 10 minutes, determined at a load of 2160 grams and at a temperature at least about 40° C. above the melting temperature of the nanoinclusion additive in accordance with ASTM D1238-13.

5. The method of claim 1, wherein the matrix polymer has a melt flow rate of from about 0.5 to about 80 grams per 10 minutes, determined at a load of 2160 grams and at a temperature at least about 40° C. above the melting temperature of the matrix polymer in accordance with ASTM D1238-13.

6. The method of claim 1, wherein extrusion occurs at a temperature of from about 180° C. to about 340° C.

7. The method of claim 1, further comprising quenching the fiber after it is passed through the spinneret.

8. The method of claim 1, wherein the fiber is a substantially continuous filament.

9. The method of claim 1, wherein the fiber has a diameter of from about 1 to about 100 micrometers.

10. The method of claim 1, wherein the nanoinclusion additive constitutes from about 0.01 wt. % to about 15 wt. % of the thermoplastic composition.

11. The method of claim 1, wherein the nanoinclusion additive contains a siloxane polymer.

12. The method of claim 1, wherein the nanoinclusion additive contains a polyepoxide.

13. The method of claim 1, wherein the nanopores have an average cross-sectional dimension of about 800 nanometers or less.

14. The method of claim 1, wherein the nanopores have an average axial dimension of from about 100 to about 5000 nanometers.

15. The method of claim 1, wherein the matrix polymer includes a polyester.

16. The method of claim 15, wherein the polyester is polyethylene terephthalate.

17. The method of claim 1, wherein the matrix polymer includes a polyolefin.

18. The method of claim 17, wherein the polyolefin is a propylene homopolymer.

19. The method of claim 1, wherein the continuous phase constitutes from about 60 wt. % to about 99 wt. % of the thermoplastic composition.

20. The method of claim 1, wherein the matrix polymer includes a polyester and wherein the continuous phase constitutes from about 60 wt. % to about 99 wt. % of the thermoplastic composition.

* * * * *